(12) United States Patent
Hieber et al.

(10) Patent No.: US 9,168,348 B2
(45) Date of Patent: Oct. 27, 2015

(54) PATIENT INTERFACE DEVICE STORAGE SYSTEM

(75) Inventors: Robert Earl Hieber, Eindhoven (NL); James Allen Hicks, Eindhoven (NL); Jonathan Paul Todd, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 263 days.

(21) Appl. No.: 13/813,986

(22) PCT Filed: Aug. 19, 2011

(86) PCT No.: PCT/IB2011/053662
§ 371 (c)(1),
(2), (4) Date: Feb. 4, 2013

(87) PCT Pub. No.: WO2012/025862
PCT Pub. Date: Mar. 1, 2012

(65) Prior Publication Data
US 2013/0139821 A1 Jun. 6, 2013

Related U.S. Application Data

(60) Provisional application No. 61/377,224, filed on Aug. 26, 2010.

(51) Int. Cl.
*A61M 16/06* (2006.01)
*A61M 16/00* (2006.01)

(52) U.S. Cl.
CPC ....... *A61M 16/0683* (2013.01); *A61M 16/0057* (2013.01); *A61M 16/06* (2013.01); *A61M 2209/06* (2013.01)

(58) Field of Classification Search
CPC ........ A62B 25/005; A62B 7/14; A62B 11/00; A62B 17/00; A62B 17/04; A62B 18/00; A62B 18/006; A62B 18/02; A62B 18/025; A62B 18/08; A62B 18/084; A62B 18/086; A62B 21/00; A62B 25/00; A62B 3/00; A62B 7/00; A62B 7/02; A62B 7/04; A62B 7/08; A62B 7/12; A62B 9/00; A62B 9/04; B64D 11/00; B64D 10/00; B64D 11/0629; B64D 13/00; B64D 13/04; B64D 25/00; A61F 17/00; A45F 3/00; A45F 3/18; A61B 19/00; A61B 19/02; A61B 19/0248; A61B 19/04; A61B 19/045; A61M 11/06; A61M 16/00; A61M 16/0057; A61M 16/06; A61M 16/0616; A61M 16/0633; A61M 16/0683
USPC .......... 128/857, 863, 200.24, 201.22, 201.23, 128/201.24, 202.27, 203.29, 204.29, 128/205.25, 206.21, 206.24, 206.27, 128/206.28, 207.13, 912; 244/118.5
See application file for complete search history.

(56) References Cited

U.S. PATENT DOCUMENTS 4,023,874 A * 5/1977 Jong et al. ................. 312/291
4,909,247 A * 3/1990 Terrisse et al. ........... 128/206.27
(Continued)

FOREIGN PATENT DOCUMENTS

WO    WO9705919 A2    2/1997

*Primary Examiner* — Annette Dixon
(74) *Attorney, Agent, or Firm* — Michael W. Haas

(57) ABSTRACT

A patient interface device storage system includes a patient interface device structured to deliver a flow of breathing gas to a patient, the patient interface device including a mask, and a storage shell having an outer peripheral wall and a bottom wall which together define a cavity. The cavity is sized and configured to receive and hold at least a portion of the mask. The bottom wall includes a first attachment member structured to be selectively engaged with a second attachment member associated with a gas delivery device in a manner such that the storage shell and the patient interface device are coupled to and held by the second attachment member.

19 Claims, 3 Drawing Sheets

(56) References Cited

U.S. PATENT DOCUMENTS

| | | | |
|---|---|---|---|
| 4,915,106 A * | 4/1990 | Aulgur et al. | 128/207.11 |
| 5,154,374 A * | 10/1992 | Beroth | 244/118.5 |
| 6,318,364 B1 * | 11/2001 | Ford et al. | 128/204.18 |
| 6,755,194 B2 * | 6/2004 | Taieb | 128/206.27 |
| 8,356,595 B2 * | 1/2013 | Schaeffer et al. | 128/204.29 |
| 2002/0007832 A1 | 1/2002 | Doherty | |
| 2002/0189617 A1 * | 12/2002 | Cordero et al. | 128/205.25 |
| 2006/0093785 A1 | 5/2006 | Hickle | |
| 2007/0045152 A1 | 3/2007 | Kwok | |
| 2009/0071480 A1 | 3/2009 | Adams | |
| 2009/0145430 A1 | 6/2009 | Hecox | |
| 2009/0151727 A1 * | 6/2009 | Schaeffer et al. | 128/205.25 |

\* cited by examiner

PATIENT INTERFACE DEVICE STORAGE SYSTEM

CROSS-REFERENCE TO RELATED APPLICATIONS

This patent application claims the priority benefit under 35 U.S.C. §371 of international patent application no. PCT/IB2011/053662, filed Aug. 19, 2011, which claims the priority benefit under 35 U.S.C. §119(e) of U.S. Provisional Application No. 61/377,224 filed on Aug. 26, 2010, the contents of which are herein incorporated by reference.

BACKGROUND OF THE INVENTION

1. Field of the Invention

The present invention relates to non-invasive ventilation therapies in which a patient interface device is used to communicate a flow with an airway of a user, and, in particular, to a transport and storage system for such a patient interface device.

2. Description of the Related Art

There are numerous situations where it is necessary or desirable to deliver a flow of breathing gas non-invasively to the airway of a patient, i.e., without intubating the patient or surgically inserting a tracheal tube. Such therapies are commonly referred to as non-invasive ventilation (NIV) therapies. For example, it is known to non-invasively deliver continuous positive airway pressure (CPAP) or variable airway pressure, which varies with the patient's respiratory cycle, to treat medical disorders, such as obstructive sleep apnea (OSA), Obesity Hypoventilation Syndrome (OHS) and Chronic Obstructive Pulmonary Disease (COPD).

NIV therapies involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. Such patient interface devices may also employ other patient contacting components, such as forehead supports, cheek pads and chin pads. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

During NIV therapy, a the patient interface device is applied and removed from the patient several times in the course of therapy. When the patient interface device is off of the patient, there is currently no controlled storage procedure. Instead, the patient interface device is often placed on a bedside table, hung from a piece of nearby equipment, or left hanging from the ventilation hose attached thereto. Such uncontrolled storage creates a heightened risk of contamination, as the environment can contaminate the patient interface device, and, in particular, the mask portion thereof, and the patient interface device, and in particular the mask portion thereof, can contaminate the environment.

In addition, NIV mask components are often packaged and shipped with a removable cover attached thereto. This cover is intended to protect the sealing cushion of the mask component from contamination and deformation during shipping. When the NIV mask component is to be put into service, this packaging is removed by the clinician and discarded. This practice is both an inconvenience to the clinician and materially wasteful.

SUMMARY OF THE INVENTION

Accordingly, it is an object of the present invention to provide a patient interface device storage system that overcomes the shortcomings of conventional techniques for transporting/handling/storing patient interface devices. This object is achieved according to one embodiment of the present invention by providing a patient interface device storage system that includes a patient interface device structured to deliver a flow of breathing gas to a patient and a storage shell. The storage shell has an outer peripheral wall and a bottom wall that together define a cavity. The cavity is sized and configured to receive and hold at least a portion of the mask. The bottom wall of the storage shell includes a first attachment member structured to be selectively engaged with a second attachment member associated with a gas delivery device in a manner wherein the storage shell and the patient interface device are coupled to and held by the second attachment member.

In another embodiment, a method of providing NIV therapy is provided that includes providing a patient interface device including a mask and a storage shell having an outer peripheral wall and a bottom wall which together define a cavity. The cavity is sized and configured to receive and hold at least a portion of the mask, and the bottom wall of the storage shell includes a first attachment member, engaging the first attachment member with a second attachment member associated with a gas delivery device in a manner such that the storage shell is coupled to and held by the second attachment member. The method further includes delivering breathing gas to a patient using the patient interface device while the patient interface device is attached to the patient, and removing the patient interface device from the patient and inserting at least a portion of the mask into the cavity in a manner wherein the patient interface device is coupled to and held by the storage shell.

In still another embodiment, a method includes providing a storage shell having an outer peripheral wall and a bottom wall that together define a cavity. The cavity is sized and configured to receive and hold at least a portion of a patient interface device. The bottom wall includes a first attachment member structured to be selectively engaged with a second attachment member associated with a gas delivery device in a manner. The shell and the patient interface device are coupled to and held by the second attachment member. The method includes inserting at least a portion of the mask into the cavity in a manner such that the patient interface device is coupled to the shell, and shipping the patient interface device coupled to the storage shell to the recipient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
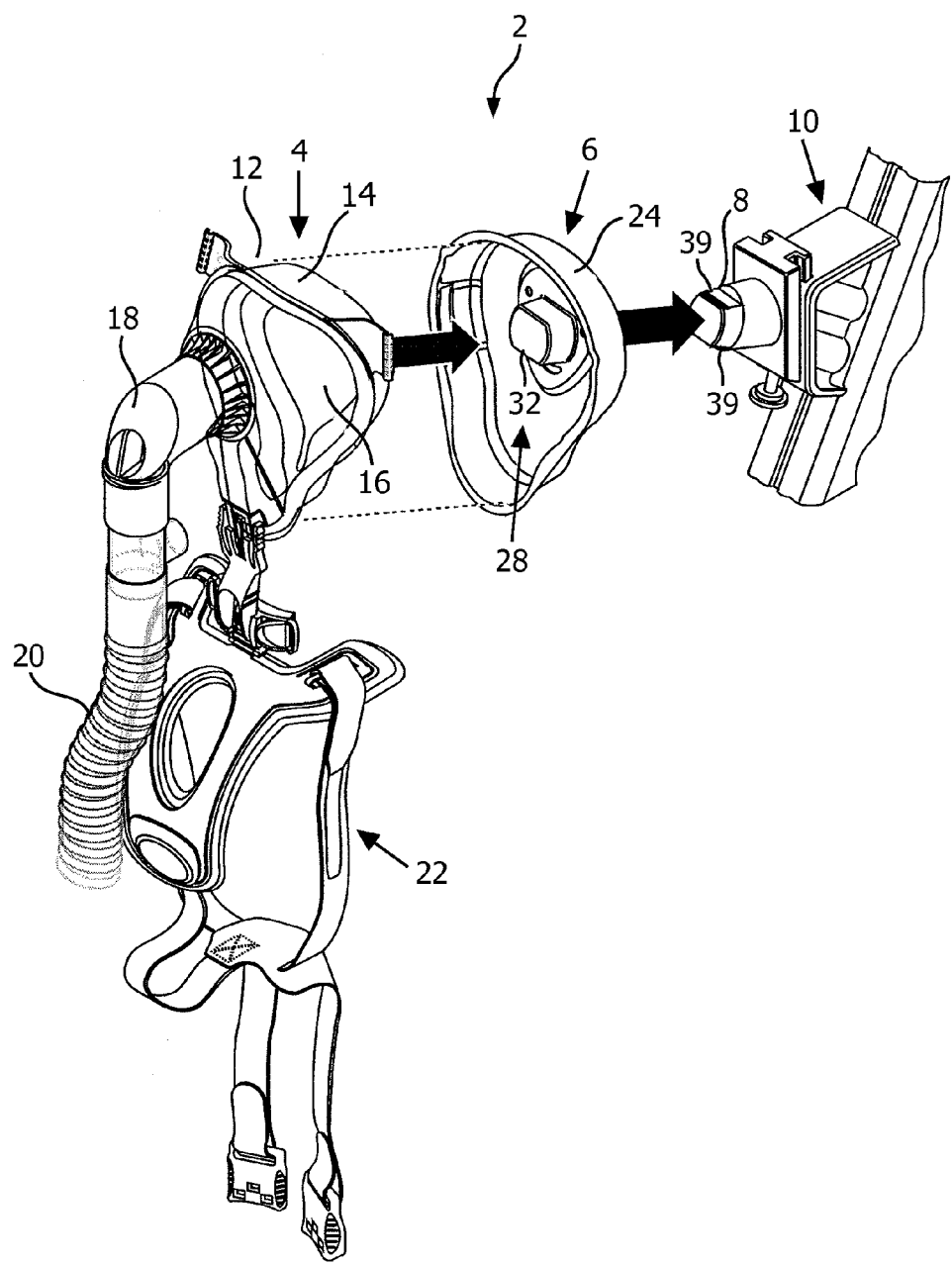
FIG. 1 is a schematic diagram of a patient interface device system according to an exemplary embodiment of the present invention.
Figure 2:
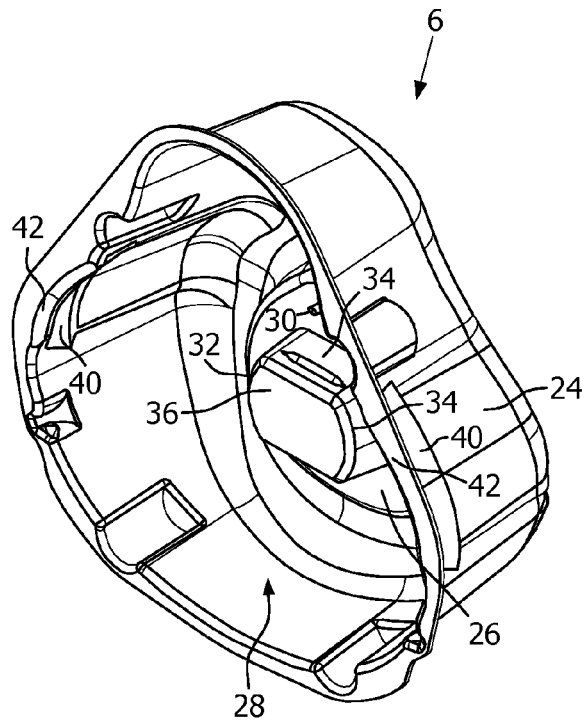
FIGS. 2, 3, 4, and 5 are front and rear isometric and front and rear elevational views, respectively, of a storage shell forming part of the system of FIG. 1 according to one exemplary embodiment of the invention.
Figure 3:
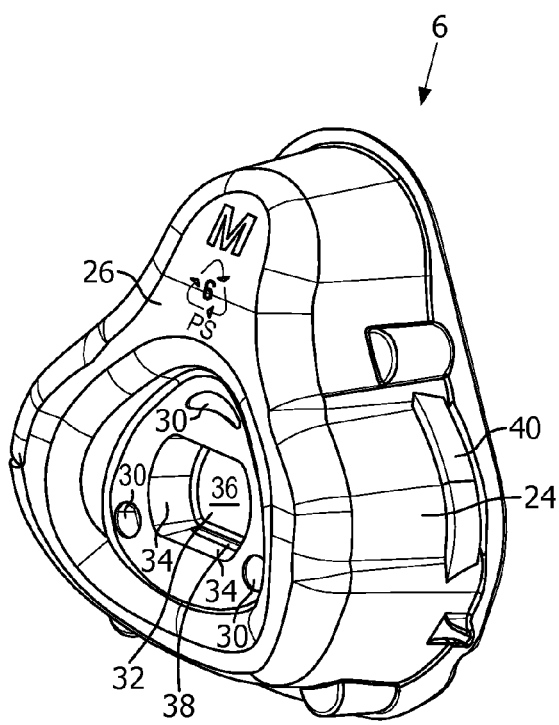
Figure 4:
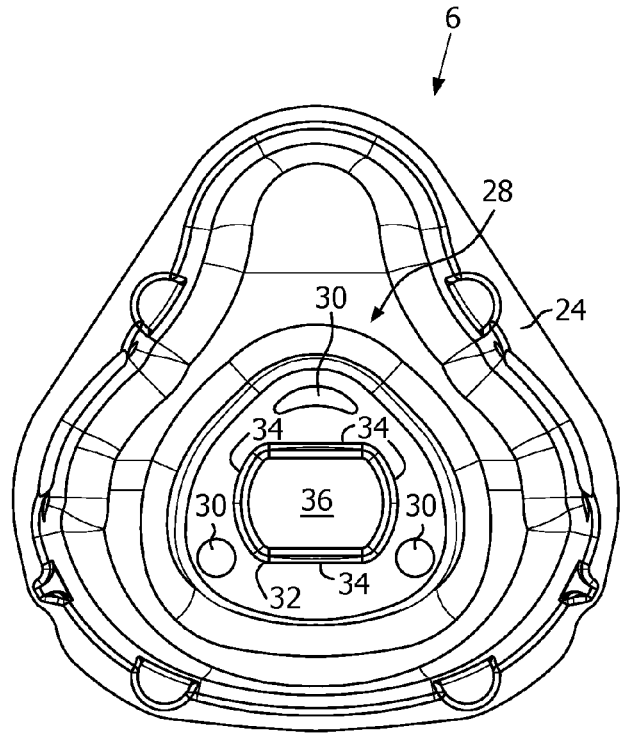
Figure 5:
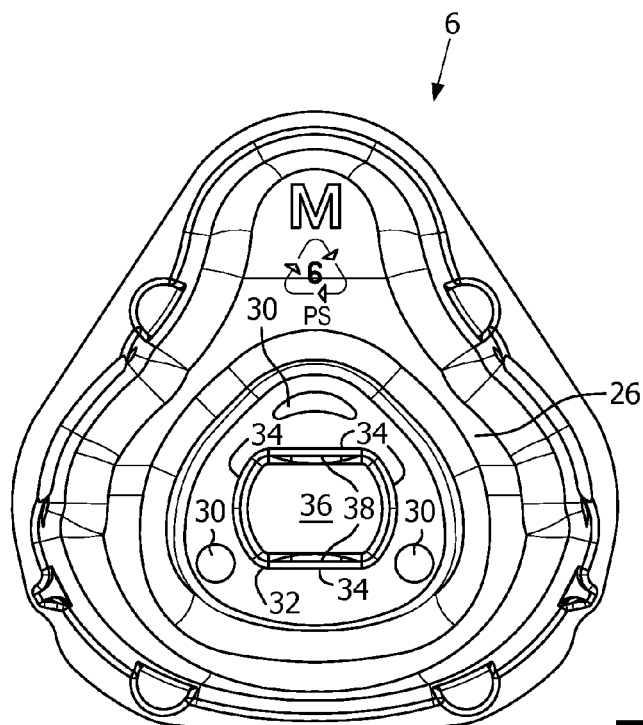

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein The present invention, in the exemplary embodiment, includes an accessory that is shipped with the mask component of an NIV patient interface device that serves two purposes. First, as described in grater detail herein, it will provide controlled, deliberate storage functionality by mounting to a component, such as a cart, associated with the gas delivery device, such as a ventilator or pressure support device, used in the NIV therapy, and serving as a receptacle or tray to hold the mask component when it is off of the patient. This controlled storage area will minimize unintended contamination between the clinical environment and the mask component, or the mask component and the clinical environment. Second, the accessory acts as a protective storage component preventing contamination and distortion of the mask component during shipping. However, its useful life will be extended beyond shipping as it will be sued to provide the storage functionality just described.

FIG. 1 is a schematic diagram of a patient interface device storage system 2 according to an exemplary embodiment of the present invention. As seen in FIG. 1, patient interface device storage system 2 includes a patient interface device 4, a storage shell 6, and an attachment member, which in the illustrated embodiment is post 8 coupled to a cart 10 that holds a breathing gas delivery device, such as a ventilator or pressure support device.

In the illustrated exemplary embodiment, patient interface device 4 includes a mask 12, which in the illustrated embodiment is a nasal/oral mask. However, other types of masks, such as a nasal mask, a nasal cushion, nasal cannula, a full face mask, or any other patient interface device that facilitates the delivery/communication of a flow of breathing gas to the airway of a patient, may be used as mask 12 while remaining within the scope of the present invention. Mask 12 includes a sealing cushion 14, which is fluidly coupled to a rigid support structure 16. In the illustrated embodiment, mask 12 has a generally triangular external shape, although other shapes are possible. Support structure 16 is fluidly coupled to an elbow conduit 18, which is coupled to a gas delivery hose 20. Support structure 16 is coupled to headgear assembly 22 for securing patient interface device 4 to the head of the patient.

FIGS. 2, 3, 4, and 5 are front and rear isometric and front and rear elevational views of storage shell 6 according to one exemplary embodiment of the invention. In the exemplary embodiment, storage shell 6 is made of a rigid or semi-rigid material such as High-Impact Polystyrene (HIPS). Storage shell 6 includes an outer peripheral wall 24 coupled to a rear wall 26, which together define an inner cavity 28. Outer peripheral wall 24 has the same general shape as the shape of the outer periphery of mask 12. Thus, in the illustrated embodiment, outer peripheral wall 24 has a generally triangular shape. Rear wall 26 includes orifices 30 extending therethrough. Rear wall 26 also includes a receptacle 32 that extends into internal cavity 28. Receptacle 32 is defined by peripheral walls 34 and a bottom wall 36. Receptacle 32 is sized, shaped and otherwise configured such is able to receive and securely hold post 8. In the illustrated embodiment, two ridges 38 extend from opposite walls 34 into the recess defined by receptacle 32. Ridges 38 on storage shell 6 engage matching channels 39 on post 8. This engagement creates a locking effect between storage shell 6 and post 8 that is stronger than the engagement between patient interface device 4 (mask 12) and storage shell 6. In other words, storage shell 6 and post 8 act as one unit during use. Removal force of shell 6 from post 8 is decidedly greater than that of mask 12 from storage shell 6.

In operation, in the exemplary embodiment, when patient interface device 4 is shipped to the location where it is to be used (e.g., a healthcare facility), patient interface device 4 is packaged in a manner wherein at least a portion of mask 12 (e.g., the sealing cushion 14) is received and held within cavity 28 of storage shell 6. In this manner, mask 12 is protected from damage and/or contamination during shipment. In the exemplary embodiment, storage shell 6 and mask 12 are sized and configured so that a snug fit between the two will result when the mask 12 or a portion thereof is inserted in cavity 28. In one particular embodiment, the snug fit is such that it will prevent mask 12 from being removed from storage shell 6 unless some degree of force is applied thereto (i.e., it will not just fall out due to gravity).

The present invention contemplates providing an engaging portion on the storage shell for securing the mask to the storage shell so that they are selectively coupled together and do not readily fall apart from one another. In the illustrated embodiment, this engaging portion is provided in the form of recessed portions 40 and lips 42 disposed on outer peripheral wall 24 of the storage shell. Portions of mask 12 will move into recessed portions 40 and lips 42 will hold mask 12 in storage shell 6 and prevent the mask from being removed from the storage shell unless some degree of force is applied thereto (i.e., it will not just fall out due to gravity).

When patient interface device 4 is received, it is stored in the same manner until it is to be used. Of course, other packing and/or shipping materials may be provided to contain the mask and storage shell. When patient interface device 4 is to be used, storage shell 6 is removed from mask 4 and the storage shell is attached to post 8. In particular, as shown in FIG. 1, storage shell 6 is attached to post 8 by causing post 8 to be inserted into and received within receptacle 32. When this is done, storage shell 6 will be securely held by post 8 in a configuration wherein cavity 28 extends outwardly. Patient interface device 4 may then be used to provide NIV therapy to the patient. When not in use, patient interface device 4 is coupled to storage shell 6 for safe storage. More specifically, as shown in FIG. 1, when patient interface device 4 is not in use, at least a portion of mask 12 (i.e., the sealing cushion 14) is inserted within cavity 28 of storage shell 6 where it may remain until it is next used. In such a storage position, mask 12 is held within cavity 28 and is surrounded by outer peripheral wall 24 coupled to rear wall 26. As a result, contamination of patient interface device 4 by the environment and/or contamination of the environment by patient interface device 4 can be reduced or eliminated. In addition, if breathing gas is still being delivered to patient interface device 4 while it is being stored in this manner (e.g., because patient interface device 4 only needs to be stored briefly while the patient is tended to), the breathing gas is able to escape from storage shell 6 through orifices 30.

The function of orifices 30 is that they permit relief of the flow and pressure developed by breathing gas delivery device at mask 12. Without orifices 30, the system could inadvertently: (i) blow the stored mask 12 off of storage shell 6, (ii) make a disruptive noise, and/or (iii) fail to alarm for "patient disconnect" (i.e.; orifices 30 ensure that the breathing gas delivery device acts properly and is not tricked into thinking mask 12 is on the patient).

The present invention contemplates that the storage shell can have a variety of configurations so long as it houses the patient interface device or at least a portion of the patient interface device. In addition, coupling members or other structures can be provided for securing the patient interface device to the storage shell.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device storage system, comprising:
   a patient interface device structured to deliver a flow of breathing gas to a patient, the patient interface device including a mask; and
   a storage shell having an outer peripheral wall and a bottom wall which together define a cavity, wherein the cavity is sized and configured to receive and hold at least a portion of the mask, and wherein the bottom wall includes a first attachment member structured to be selectively engaged with a second attachment member associated with a gas delivery device in a manner wherein the storage shell and the patient interface device are coupled to and held by the second attachment member, wherein the first attachment member comprises a receptacle sized and configured to receive the second attachment member therein, and wherein the second attachment member is a post provided on a cart associated with the gas delivery device.

2. The patient interface device storage system according to claim 1, wherein the outer peripheral wall has a first shape and an outer periphery of the mask has a second shape that is generally the same as the first shape.

3. The patient interface device storage system according to claim 1, wherein receptacle extends inwardly from the bottom wall and into the cavity.

4. The patient interface device storage system according to claim 1, wherein one or more orifices are provided in the bottom wall.

5. The patient interface device storage system according to claim 1, wherein the mask is a nasal mask, a nasal cushion, nasal/oral mask or a full face mask.

6. The patient interface device storage system according to claim 1, wherein the mask includes a cushion, wherein the storage shell is structured to cover at least the cushion when the at least a portion of the mask is received in the cavity.

7. The patient interface device storage system according to claim 1, further comprising an engaging portion provided on the storage shell to selectively couple the mask to the storage shell.

8. A method of providing non-invasive ventilation therapy, comprising:
   providing a patient interface device including a mask;
   providing a storage shell having an outer peripheral wall and a bottom wall which together define a cavity, wherein the cavity is sized and configured to receive and hold at least a portion of the mask, and wherein the bottom wall includes a first attachment member, wherein the first attachment member comprises a receptacle sized and configured to receive the second attachment member therein;
   engaging the first attachment member with a second attachment member associated with a gas delivery device in a manner wherein the storage shell is coupled to and held by the second attachment member, wherein the second attachment member is a post provided on a cart associated with the gas delivery device;
   delivering breathing gas to a patient using the patient interface device while the patient interface device is attached to the patient; and
   removing the patient interface device from the patient and inserting at least a portion of the mask into the cavity in a manner wherein the patient interface device is coupled to and held by the storage shell.

9. The method according to claim 8, wherein the outer peripheral wall has a first shape and an outer periphery of the mask has a second shape that is generally the same as the first shape.

10. The method according to claim 8, wherein receptacle extends inwardly from the bottom wall and into the cavity.

11. The method according to claim 8, wherein one or more orifices are provided in the bottom wall.

12. The method according to claim 8, wherein the mask includes a cushion, wherein the storage shell covers at least the cushion when the at least a portion of the mask is inserted into the cavity.

13. The method according to claim 8, further comprising an engaging portion provided on the storage shell to selectively couple the mask to the storage shell.

14. A method providing a patient interface device including a mask to a recipient, comprising:
   providing a storage shell having an outer peripheral wall and a bottom wall which together define a cavity, wherein the cavity is sized and configured to receive and hold at least a portion of the mask, and wherein the bottom wall includes a first attachment member structured to be selectively engaged with a second attachment member associated with a gas delivery device in a manner wherein the storage shell and the patient interface device are coupled to and held by the second attachment member, wherein the first attachment member comprises a receptacle sized and configured to receive the second attachment member therein, and wherein the second attachment member is a post provided on a cart associated with the gas delivery device;

inserting at least a portion of the mask into the cavity in a manner wherein the patient interface device is coupled to the storage shell; and shipping the patient interface device coupled to the storage shell to the recipient.

15. The method according to claim 14, wherein the mask includes a cushion, wherein the storage shell covers at least the cushion when the at least a portion of the mask is inserted into the cavity.

16. The method according to claim 14, wherein the outer peripheral wall has a first shape and an outer periphery of the mask has a second shape that is generally the same as the first shape.

17. The method according to claim 14, wherein receptacle extends inwardly from the bottom wall and into the cavity.

18. The method according to claim 14, wherein one or more orifices are provided in the bottom wall.

19. The method according to claim 14, further comprising an engaging portion provided on the storage shell to selectively couple the mask to the storage shell.

* * * * *